US012648784B2

(12) United States Patent
Gifford, III et al.

(10) Patent No.: US 12,648,784 B2
(45) Date of Patent: Jun. 9, 2026

(54) MECHANICAL VENOUS CLOT RETRIEVAL

(71) Applicant: The Foundry, LLC, Menlo Park, CA (US)

(72) Inventors: Hanson S. Gifford, III, Woodside, CA (US); Edward DeWitt Gifford, Glastonbury, CT (US)

(73) Assignee: The Foundry, LLC, Menlo Park, CA (US)

( * ) Notice: Subject to any disclaimer, the term of this patent is extended or adjusted under 35 U.S.C. 154(b) by 0 days.

(21) Appl. No.: 19/274,341

(22) Filed: Jul. 18, 2025

(65) Prior Publication Data

US 2025/0345081 A1 Nov. 13, 2025

Related U.S. Application Data

(63) Continuation of application No. 17/250,606, filed as application No. PCT/US2019/045941 on Aug. 9, 2019, now Pat. No. 12,364,495.

(60) Provisional application No. 62/717,077, filed on Aug. 10, 2018.

(51) Int. Cl.
*A61B 17/221* (2006.01)
*A61B 17/22* (2006.01)

(52) U.S. Cl.
CPC .. *A61B 17/221* (2013.01); *A61B 2017/22038* (2013.01)

(58) Field of Classification Search
CPC ........ A61B 17/221; A61B 2017/22038; A61B 17/320725; A61B 2017/22034; A61B 2017/22067
See application file for complete search history.

(56) References Cited

U.S. PATENT DOCUMENTS

| | | | |
|---|---|---|---|
| 5,192,286 A | 3/1993 | Phan et al. | |
| 5,902,263 A * | 5/1999 | Patterson ....... | A61B 17/320758 |
| | | | 606/159 |
| 5,972,019 A | 10/1999 | Engelson et al. | |
| 11,877,752 B2 | 1/2024 | Walzman | |

(Continued)

FOREIGN PATENT DOCUMENTS

| | | |
|---|---|---|
| CN | 101180006 A | 5/2008 |
| CN | 101301218 A | 11/2008 |

(Continued)

OTHER PUBLICATIONS

Extended European Search Report dated Nov. 20, 2024 in EP Patent Appl. Serial No. 24199032.4.
International Search Report and Written Opinion mailed Oct. 24, 2019; International Application No. PCT/US2019/045941.

*Primary Examiner* — Kathleen S Holwerda
*Assistant Examiner* — James R McGinnity
(74) *Attorney, Agent, or Firm* — Greenberg Traurig, LLP; Christopher C. Bolten; Albert K. Heng

(57) ABSTRACT

Systems and methods are provided for removal of clot material from a treatment site in a blood vessel, particularly in venous vasculature. A treatment device can include a core member having a distal portion and an inner coil surrounding the distal portion of the core member. A helical outer member surrounds at least a portion of the inner coil, and a sheet of flexible material extends between the inner coil and the helical outer member, such that the sheet extends helically around the inner coil to provide a surface for clot engagement at the treatment site.

23 Claims, 6 Drawing Sheets

(56)     References Cited

U.S. PATENT DOCUMENTS

| | | |
|---|---|---|
| 12,364,495 B2 | 7/2025 | Gifford, III et al. |
| 2001/0031981 A1 * | 10/2001 | Evans ............ A61B 17/320725 |
| | | 606/159 |
| 2002/0173819 A1 | 11/2002 | Leeflang et al. |
| 2003/0144685 A1 | 7/2003 | Boyle et al. |
| 2004/0088000 A1 | 5/2004 | Muller |
| 2005/0283166 A1 | 12/2005 | Greenhalgh |
| 2006/0184194 A1 | 8/2006 | Pal et al. |
| 2009/0240238 A1 | 9/2009 | Grodrian et al. |
| 2011/0125132 A1 | 5/2011 | Krolik et al. |
| 2012/0022579 A1 | 1/2012 | Fulton |
| 2016/0367285 A1 * | 12/2016 | Sos ...................... A61B 17/221 |
| 2018/0014840 A1 | 1/2018 | Panian |
| 2018/0093080 A1 | 4/2018 | Krolik et al. |
| 2019/0167287 A1 | 6/2019 | Vale et al. |
| 2022/0287817 A1 | 9/2022 | Garrison et al. |
| 2025/0099120 A1 | 3/2025 | Lagoe et al. |

FOREIGN PATENT DOCUMENTS

| | | |
|---|---|---|
| CN | 102665815 A | 9/2012 |
| CN | 103200886 A | 7/2013 |
| CN | 104042304 A | 9/2014 |
| CN | 104159525 A | 11/2014 |
| CN | 104582608 A | 4/2015 |
| CN | 105102052 A | 11/2015 |
| CN | 105208950 A | 12/2015 |
| JP | 2006055634 A | 3/2006 |
| JP | 2011526820 A | 10/2011 |
| JP | 2013500082 A | 1/2013 |
| JP | 2016513524 A | 5/2016 |
| JP | 2016521169 A | 7/2016 |
| JP | 6509259 B2 | 5/2019 |
| WO | WO-2009046206 A1 | 4/2009 |

* cited by examiner

105

113

CM

123

101

MECHANICAL VENOUS CLOT RETRIEVAL

CROSS-REFERENCE TO RELATED APPLICATIONS

This application is a continuation of U.S. patent application Ser. No. 17/250,606, filed Feb. 10, 2021, now U.S. Pat. No. 12,364,495, which is a 371 U.S. national phase application of International PCT Patent Application No. PCT/US2019/045941, filed Aug. 9, 2019, which claims the benefit of priority of U.S. Provisional Application No. 62/717,077, filed Aug. 10, 2018, the entire contents of each of which are incorporated herein by reference.

TECHNICAL FIELD

The present technology relates to the removal and/or retrieval of blood clots via mechanical extraction from within a blood vessel lumen.

BACKGROUND

Venous thromboembolic disease represents a major source of post-traumatic, post-partum and in-hospital acquired morbidity and mortality. Clots that originate as Deep Vein Thromboses (DVT) in the lower extremity and less often in the upper extremity can cause limb swelling, tissue gangrene, chronic destruction of the venous valve system and long-term chronic conditions such as limb fatigue, edema and heaviness (collectively referred to as Post-Thrombotic Syndrome, PTS). This represents a major detriment to quality of life amongst patients who develop a large DVT. Furthermore, a clot that develops in the upper or lower extremities poses a risk of clot migration that can lead to Pulmonary Embolism (PE). Current therapies for both DVT and PE that do not improve with conservative management (leg elevation, compression, systemic heparinization) predominantly revolve around thrombolysis, or destruction of the clot with potent intravenous and intra-arterial medications. These can be used in conjunction with rheolytic mechanical thrombectomy that further attempts to dissolve the offending blood clot.

Conventional approaches to treating DVT and/or PE include clot reduction and/or removal. For example, anticoagulants can be introduced to the affected vessel to prevent additional clots from forming, and thrombolytics can be introduced to the vessel to at least partially disintegrate the clot. However, such agents typically take a prolonged period of time (e.g., hours, days, etc.) before the treatment is effective and in some instances can cause hemorrhaging. Transcatheter clot removal devices also exist, however, such devices are typically highly complex, prone to cause trauma to the vessel, hard to navigate to the pulmonary embolism site, and/or expensive to manufacture. Most of the current therapeutic approaches to DVT and PE involve hospital stays of multiple days—with common intensive care unit (ICU) stays of 12-72 hours if catheter-based thrombolysis is employed. Clot removal by destruction—either mechanical or via thrombolysis, has little to no effect on chronic scar tissue, or fibrin, that may narrow the patent vessel diameter and lead to early re-accumulation of clot or re-stenosis of venous stents. To date there are no devices that specifically target removal of chronic fibrin from the intravenous system.

Accordingly, there is a need for improved systems and methods for treatment of deep vein thrombosis and/or pulmonary embolism.

SUMMARY

Embodiments of the present technology are directed to systems and methods for treatment of deep vein thrombosis and/or pulmonary embolism. The subject technology is illustrated, for example, according to various aspects described below, including with reference to FIGS. 1-5. Various examples of aspects of the subject technology are described as numbered clauses (1, 2, 3, etc.) for convenience. These clauses can be combined with one another in any order and in any combination. These are provided as examples and do not limit the subject technology.

Clause 1. A device for treatment of deep vein thrombosis or pulmonary embolism, the device comprising: a core member having a distal portion; an inner member surrounding the distal portion of the core member, the inner member being slidably extendable along the core member distal portion; a helical outer member surrounding at least a portion of the inner member; and a flexible material extending between the inner member and the helical outer member.

Clause 2. The device of any one of the preceding Clauses, wherein the helical outer member has a compressed configuration for delivery through a catheter and an uncompressed configuration for deployment at a treatment site in a blood vessel, wherein in the uncompressed configuration, the helical outer member has a greater radial dimension and a smaller axial dimension than in the compressed configuration Clause 3. The device of any one of the preceding Clauses, wherein the flexible material comprises a sheet with one or more apertures formed therein.

Clause 4. The device of any one of the preceding Clauses, wherein the one or more apertures define baffles in the sheet.

Clause 5. The device of any one of the preceding Clauses, wherein the baffles are configured to engage clot material at the treatment site.

Clause 6. The device of any one of the preceding Clauses, wherein a distal portion of the flexible material defines a closed-cell filter.

Clause 7. The device of any one of the preceding Clauses, wherein the closed-cell filter is configured to prevent distal embolization of clot material.

Clause 8. The device of any one of the preceding Clauses, wherein the flexible material comprises a polymer.

Clause 9. The device of any one of the preceding Clauses, wherein the polymer comprises at least one of: urethane, polyethylene, expanded polytetrafluoroethylene (EPTFE), or polyethylene terephthalate (PET).

Clause 10. The device of any one of the preceding Clauses, wherein the inner member comprises a coil having a first pitch in an unconstrained state, wherein the helical outer member has a second pitch in the uncompressed configuration, and wherein the second pitch is greater than the first pitch.

Clause 11. The device of any one of the preceding Clauses, wherein the device has a low-profile configuration for advancement through a delivery sheath, and an expanded configuration for deployment at the treatment site.

Clause 12. The device of any one of the preceding Clauses, wherein the helical outer member has a proximal end portion coupled to the inner member at a first point and a distal end portion coupled to the inner member at a second point.

Clause 13. The device of any one of the preceding Clauses, wherein the core member comprises a polymer tube configured to be slidably advanced over a guidewire.

Clause 14. The device of any one of the preceding Clauses, wherein the inner member comprises a metallic wire coil.

Clause 15. The device of any one of the preceding Clauses, wherein the inner member comprises a shape-memory material.

Clause 16. The device of any one of the preceding Clauses, wherein the inner member comprises stainless steel or nitinol.

Clause 17. The device of any one of the preceding Clauses, wherein the helical outer member comprises a metallic wire.

Clause 18. The device of any one of the preceding Clauses, wherein the helical outer member comprises a shape-memory material.

Clause 19. The device of any one of the preceding Clauses, wherein the helical outer member comprises stainless steel or nitinol.

Clause 20. The device of any one of the preceding Clauses, wherein the helical outer member has a curved radially outer surface configured to abut a vessel wall and a sharp radially inward edge configured to engage clot material.

Clause 21. The device of any one of the preceding Clauses, wherein the sharp radially inner edge is configured to facilitate separating the clot material from the vessel wall.

Clause 22. A system for treatment of deep vein thrombosis or pulmonary embolism, the system comprising: a covering sheath having a lumen; a treatment device configured to be slidably received within the lumen for advancement to a treatment site, the treatment device comprising: a core member having a distal portion; an inner member surrounding the distal portion of the core member; a helical outer member surrounding at least a portion of the inner member, the helical outer member having a low-profile configuration for delivery through a catheter and an expanded configuration for deployment at the treatment site; and a flexible material extending between the inner coil and the helical outer member.

Clause 23. The system of any one of the preceding Clauses, wherein the covering sheath has a diameter of approximately 6-9 Fr.

Clause 24. The system of any one of the preceding Clauses, further comprising a delivery sheath having a lumen configured to slidably receive the covering sheath therein.

Clause 25. The system of any one of the preceding Clauses, wherein the delivery sheath has a diameter of approximately 12-14 Fr.

Clause 26. The system of any one of the preceding Clauses, wherein the delivery sheath comprises an expandable member disposed at a distal portion thereof.

Clause 27. The system of any one of the preceding Clauses, wherein the expandable member comprises an expandable braided tip.

Clause 28. The system of any one of the preceding Clauses, further comprising a guidewire, and wherein the core member comprises a polymer tube configured to be slidably advanced over the guidewire.

Clause 29. A device for treatment of deep vein thrombosis or pulmonary embolism, the device comprising: a core member configured to be positioned intravascularly at or adjacent a treatment site; an inner member coupled to the core member, the inner member configured to transition from a first axial length to a second axial length greater than the first; an outer member spirally winding around at least a portion of the inner member, the outer member having a low-profile configuration for delivery through a catheter and an expanded configuration for deployment at the treatment site; and a flexible material extending between the inner member and the outer member, the flexible material configured to engage clot material when the outer member is in the expanded configuration.

Clause 30. The device of any one of the preceding Clauses, wherein the inner member comprises a coil.

Clause 31. The device of any one of the preceding Clauses, wherein the inner member comprises a hypotube.

Clause 32. The device of any one of the preceding Clauses, wherein the inner member is stretchable.

Clause 33. The device of any one of the preceding Clauses, wherein the inner member comprises a plurality of discrete elements axially spaced apart along the core member.

Clause 34. The device of any one of the preceding Clauses, wherein the outer member comprises a helically winding wire.

Clause 35. The device of any one of the preceding Clauses, wherein the outer member comprises a shape-memory material.

Clause 36. The device of claim 28, wherein the outer member has a curved radially outer surface configured to abut a vessel wall and a sharp radially inward edge configured to engage clot material.

Clause 37. The device of any one of the preceding Clauses, wherein the sharp radially inner edge is configured to facilitate separating the clot material from the vessel wall.

Clause 38. The device of any one of the preceding Clauses, wherein the flexible material comprises a sheet with one or more apertures formed therein.

Clause 39. The device of any one of the preceding Clauses, wherein one or more of the apertures are lined with a reinforcing material.

Clause 40. The device of any one of the preceding Clauses, wherein the reinforcing material comprises a metallic material.

Clause 41. The device of any one of the preceding Clauses, wherein the one or more apertures define baffles in the sheet.

Clause 42. The device of any one of the preceding Clauses, wherein the baffles are configured to engage clot material at the treatment site.

Clause 43. The device of any one of the preceding Clauses, wherein a distal portion of the flexible material defines a closed-cell filter.

Clause 44. The device of any one of the preceding Clauses, wherein the closed-cell filter is configured to prevent distal embolization of clot material.

Clause 45. The device of any one of the preceding Clauses, wherein the flexible material comprises a polymer.

Clause 46. The device of any one of the preceding Clauses, wherein a length of the outer member is greater in the low-profile configuration than in the expanded configuration.

Clause 47. The device of any one of the preceding Clauses, wherein the length of the outer member is at least twice as great in the low-profile configuration as in the expanded configuration.

Clause 48. The device of any one of the preceding Clauses, wherein a distal end portion of the outer member is coupled to the inner member at a first point and a proximal end portion of the outer member is coupled to the inner member at a second point.

Clause 49. The device of any one of the preceding Clauses, wherein, when the outer member transitions from the low-profile configuration to the expanded configuration, the first point and the second point move closer together.

Clause 50. The device of any one of the preceding Clauses, wherein, when the outer member transitions from the expanded configuration to the low-profile configuration, the first point and the second point move further apart.

Clause 51. The device of any one of the preceding Clauses, wherein the core member is configured to be slidably advanced over a guidewire.

Clause 52. A method for removing clot material from a vessel lumen, the method comprising: advancing the device of any one of the preceding Clauses to a treatment site in the vessel lumen; and engaging clot material with the device.

Clause 53. A method for removing a clot material from a vessel lumen, the method comprising: advancing a treatment device disposed in a covering sheath through the vessel lumen to a treatment site adjacent the clot material, wherein the treatment device comprises: a core member having a distal portion; an inner member surrounding the distal portion of the core member; a helical outer member surrounding at least a portion of the inner coil; and a flexible material extending between the inner member and the helical outer member, wherein the helical outer member is in a low-profile configuration while disposed in the covering sheath; and releasing the treatment device from the covering sheath, thereby expanding the helical outer member from the low-profile configuration into an expanded configuration.

Clause 54. The method of any one of the preceding Clauses, wherein releasing the treatment device from the covering sheath comprises retracting the covering sheath with respect to the treatment device.

Clause 55. The method of any one of the preceding Clauses, wherein the covering sheath has a diameter of approximately 6-9 Fr.

Clause 56. The method of any one of the preceding Clauses, wherein releasing the treatment device causes the helical outer member to engage the clot material.

Clause 57. The method of any one of the preceding Clauses, wherein releasing the treatment device causes the helical outer member to penetrate the clot material.

Clause 58. The method of any one of the preceding Clauses, wherein, after expanding the helical outer member from the low-profile configuration into the expanded configuration, the flexible material extends helically through the clot material.

Clause 59. The method of any one of the preceding Clauses, wherein expanding the helical outer member causes at least a portion of the clot material to be engaged between adjacent spirals of the helical outer member.

Clause 60. The method of any one of the preceding Clauses, wherein the flexible material comprises apertures, and wherein, after expanding the helical outer member from the low-profile configuration into the expanded configuration, at least a portion of the clot material extends through one or more of the apertures.

Clause 61. The method of any one of the preceding Clauses, further comprising, after releasing the treatment device from the covering sheath, retracting the treatment device into a surrounding delivery sheath.

Clause 62. The method of any one of the preceding Clauses, wherein retracting the treatment device into the surrounding delivery sheath comprises dislodging at least a portion of the clot material.

Clause 63. The method of any one of the preceding Clauses, wherein retracting the treatment device into the surrounding delivery sheath comprises removing at least a portion of the clot material.

Clause 64. The method of any one of the preceding Clauses, wherein the surrounding delivery sheath comprises an expandable tip, and wherein the expandable tip is in the expanded state while the treatment device is retracted into the surrounding delivery sheath.

Clause 65. The method of any one of the preceding Clauses, wherein expanding the helical outer member causes at least a portion of the helical outer member to contact a vessel wall.

Clause 66. The method of any one of the preceding Clauses, wherein expanding the helical outer member comprises expanding a distal embolic filter coupled to the helical outer member.

Clause 67. The method of any one of the preceding Clauses, further comprising twisting the treatment device after releasing the treatment device from the covering sheath.

Clause 68. The method of any one of the preceding Clauses, wherein twisting the treatment device comprises manipulating a torque device engaged with a proximal portion of the treatment device.

Clause 69. The method of any one of the preceding Clauses, wherein releasing the treatment device from the covering sheath comprises releasing the treatment device in sequential stages.

Clause 70. A system for staged compression of a clot prior to removal from the body over an endovascular system, the system configured to: prevent distal embolization; allow continuous hemostasis via an outer treatment sheath; and/or allow for multiple treatments to occur and maximize clot removal.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1:
FIG. 1 illustrates a treatment system in accordance with aspects of the present technology.

Embodiments of the present technology are directed to systems and methods for treatment of deep vein thrombosis and/or pulmonary embolisms. Specific details of several embodiments of the technology are described below with reference to FIGS. 1-5.

In accordance with some embodiments, a treatment device as described herein can be used for clot removal of upper and lower extremity venous blood clots, and/or for clot removal from pulmonary arteries secondary to pulmonary embolism. The treatment device can be inserted over a guidewire via peripheral venipuncture in the upper or lower extremities, or via venipuncture of the internal jugular vein. The treatment device may also be used in any other vein or artery of the circulatory system where clot or other occlusive material is desired to be removed.

The device can be configured to engage the clot and remove it via simple deployment and removal by a physician, without the need for complicated techniques or training. In some embodiments, the device is configured to engage a clot which might fill a relatively large vessel, and to divide and linearize that clot into a longer, smaller-diameter form so that it can be removed through a sheath which is smaller than that large vessel.

In some embodiments, the treatment system allows a clinician to provide continuous hemostasis over a surrounding sheath during the procedure. By providing a delivery sheath with an expandable tip, the entire assembly (including the clot, the treatment device, the covering sheath, and the delivery sheath) can be removed with a profile of between 12-14 Fr. This allows all the treatments to be performed through a larger (e.g., 16-18 French) access sheath. Thus clot material can be removed via repeated treatments without dilating the vein at the access site. The outer access sheath remains intact, preventing unnecessary blood loss.

As described in more detail below, in some embodiments the treatment device can include an inner member such as a coil mounted over a tube and an outer member such as a helically extending wire that surrounds the inner member. The outer member can be a shape-memory material that can assume a compressed, low-profile configuration for delivery and an expanded, deployed configuration with a larger radial dimension for engagement with a blood clot. A flexible material such as a polymer sheet can extend between the inner member and the outer member along at least a portion of their respective lengths. In the deployed state, the flexible material can extend into and adjacent the blood clot material to engage the blood clot material and facilitate its extraction and removal. The flexible material can have apertures that define baffles to provide improved engagement with the clot material.

Example Treatment Systems

The treatment devices disclosed herein can be provided as one part of a treatment system, which includes: a treatment device 101, a covering sheath 103, an elongated delivery sheath 105, which may have an expandable braided tip 106 that can expand to accommodate a clot in the process of retrieval, and an atraumatic steerable guidewire 107.

In some embodiments, the covering sheath 103 is slidably received within a lumen of the delivery sheath 105. The treatment device can be slidably received within the lumen of the covering sheath, and a guidewire 107 can be slidably received within a lumen of the treatment device. In some embodiments, the delivery sheath 105 can have a nominal diameter of approximately 12-14 Fr, and the covering sheath 103 can have a nominal diameter of between about 6-9 Fr, or approximately 8 Fr. The delivery sheath 105 can have an expandable tip 106 (e.g., a 2 cm braided tip) at its distal portion, for example a braid or a balloon that can be expanded into apposition against a surrounding vessel wall. In some embodiments, the covering sheath 103 can have an expandable tip (e.g., a 2 cm braided tip) disposed at its distal portion.

According to some embodiments, the bodies of the delivery sheath 105 and/or the covering sheath 103 can be made from various thermoplastics, e.g., polytetrafluoroethylene (PTFE or TEFLON®), fluorinated ethylene propylene (FEP), high-density polyethylene (HDPE), polyether ether ketone (PEEK), Polyether block amide (PEBAX), etc., which can optionally be lined on the inner surface or an adjacent surface with a hydrophilic material such as polyvinylpyrrolidone (PVP) or some other plastic coating. Additionally, either surface can be coated with various combinations of different materials, depending upon the desired results.

FIG. 1 illustrates a treatment system 100, which includes a treatment device 101 slidably received within a surrounding covering sheath 103 and a larger-diameter delivery sheath 105. As noted above, the covering sheath 103 can have a diameter of between about 6-9 Fr, or approximately 8 Fr. This would be used to deliver the treatment device 101 through the clot, as described in more detail below. The covering sheath 103 may remain proximal to the functional section of the treatment device 101 as tension is applied to the shaft of the treatment device 101 to draw the clot into the larger-diameter delivery sheath 105. As noted above, the delivery sheath 105 can have a diameter of approximately 12-14 Fr in some embodiments, and may optionally include an expandable tip 106 (e.g., a 2 cm braided tip) capable of further capturing and compressing the clot to allow for seamless extraction.

Example Treatment Devices

A treatment device 101 (e.g., a treatment catheter) can include an elongated tubular shaft having a distally located functional portion 109. As noted above, the treatment device 101 can be slidably advanced over a guidewire, and can also be slidably received within a surrounding covering sheath 103 and/or delivery sheath 105 for advancement to a treatment site. While in the covering sheath 103, the functional portion 109 of the treatment device 101 can be restrained in a compressed, unexpanded, linearized, and/or low-profile configuration. Upon release from the covering sheath, the functional portion 109 of the treatment device 101 can assume an uncompressed, expanded, deployed, and/or helical configuration having a greater radially outermost dimension than in the compressed state.

The functional portion 109 of the treatment device 101 can include one or more helically extending elements separated transversely by a flexible material such as a polyurethane sheet. The flexible material may be substantially continuous or can include one or more apertures along its length. The helically extending elements together may cause the functional portion 109 of the treatment device 101 to tend towards a pre-formed, generally spiral or helical shape. After deployment in a blood vessel of a human patient, the functional portion 109 of the treatment device 101 is transformable between a delivery state having a low profile that is configured to pass through the vasculature and a deployed state having a radially expanded shape (e.g., generally spiral/helical or coil shape) in which the helically extending elements maintain the assembly in stable apposition with an inner wall of the target blood vessel.

As illustrated in FIG. 1, the functional portion 109 of the treatment device 101 includes a coiled inner member 111 spirally wound around a central core member 115. A helical outer member 113 spirally winds around and surrounds the coiled inner member 111 and the central tubular member. The coiled inner member 111 and/or the helical outer member 113 can be made of nitinol, stainless steel, rigid polymers, or other suitable material. In some embodiments, the diameter of the helical outer member 113 in the expanded state is approximately the same as the diameter of the vein or vessel at the treatment site. In some embodiments, the helical outer member 113 has a diameter in the expanded, unconstrained state of around 12-14 mm, but may also function if constrained by smaller diameter vessels or due to engagement with clot material. Alternatively, the helical outer member 113 can be provided in different sizes for different target vessels.

The helical outer member 113 and the coiled inner member 111 can be bonded together at the proximal and distal ends of the functional portion 109 of the device. The core member 115 can be an elastic polymer tube having a lumen that allows passage over a guidewire (e.g., over a minimum a 0.035" guidewire). As illustrated, the helical outer member 113 can have a significantly greater pitch than the more tightly wound coiled inner member 111. In some embodiments, the coiled inner member 111 can be configured such that extension and contraction of the coiled inner member 111 does not substantially alter a radial dimension of the coiled inner member 111. In contrast, the helical outer member 113 can be configured such that, when elongated, the helical outer member 113 assumes a reduced radial dimension, for example fully or partially linearizing such that the outer member 113 runs substantially parallel to the core member 115. When the helical outer member 113 is compressed or is released from elongation, it may assume a deployed configuration with an increased radial dimension as shown in FIG. 1. In some embodiments, the length of the functional portion 109 is approximately 80 mm when unconstrained in the expanded, deployed configuration. When linearized within the covering sheath 103, the helical outer member 113 and the coiled inner member 111 may increase in length by between 50-100% of the unconstrained length.

A sheet 117 of flexible material is coupled to both the coiled inner member 111 and the helical outer member 113 of the treatment device 101. The sheet 117 can be made of a polymer, for example urethane, polyethylene, expanded polytetrafluoroethylene (EPTFE), polyethylene terephthalate (PET), or other biocompatible polymer. It may also be made of a flexible metal mesh or screen, such as a fine nitinol or stainless steel mesh. In some embodiments, the sheet 117 can be attached to the helical outer member 113 while it is in an extended (e.g., linearized) state, such that when the helical outer member 113 assumes a helical or spiral configuration (such as during device deployment), the sheet 117 also forms a spiral helical strip. In some embodiments, the sheet may have one or more apertures 119 (e.g., pores, perforations, slices, segments, twists, cups, or other features) along its length to allow it to engage the clot when it is deployed. In some embodiments, the apertures may fully separate adjacent portions of the sheet 117 such that the sheet 117 includes multiple discrete sections extending between the inner member 111 and the outer member 113. The remaining material defined by the apertures 119 can form baffles 121 configured to engage clot material. In some embodiments, a distal portion of the sheet has no apertures, thereby forming a closed-cell filter 123. This filter 123 can prevent distal embolization of clot material to more central veins, main pulmonary arteries, or sub-segmental pulmonary arteries.

In some embodiments, the treatment device 101 may be used in conjunction with intravenous or intra-arterial thrombolytic medication, while in other embodiments the treatment device 101 is configured to perform mechanical thrombectomy without the need for adjunctive care.

In some embodiments, a mechanism at the proximal end of the treatment device 101 may be provided to automate the deployment of the treatment device 101 to allow for a staged-ratio deployment, such that, for example, for every one centimeter of covering sheath 103 withdrawal, three centimeters of the treatment device 101 are exposed. This may optimize the radial expansion of the helical outer member 113 to ensure maximum contact with the vessel wall at the location of the thrombus, and thus maximum clot retrieval per treatment iteration.

In some embodiments, baffles 121 formed in the sheet 117 can be bolstered or manufactured with smaller radially directed nitinol wires that would allow for maximum envelopment of the central blood clot. This could in turn maximize clot compression for final extraction.

In situations where clot retrieval includes a substantial burden of chronic clot, in the form of fibrin, a plastic coating to the helical outer member 113 can act as an outer soft protecting edge to protect the vessel wall, with an inner cutting edge such that if the device 101 is rotated it can separate the chronic fibrin from the vessel wall to facilitate clot retrieval.

An alternative embodiment of the treatment device 101 may obviate the polymer baffles 121, using a simple helical outer member 113, affixed proximally and distally to a central guidewire or other centrally disposed anchoring member. In such a case, an open-cell or closed-cell embolic protection cap may optionally be positioned at the distal-most aspect of the device 101.

Figure 6:
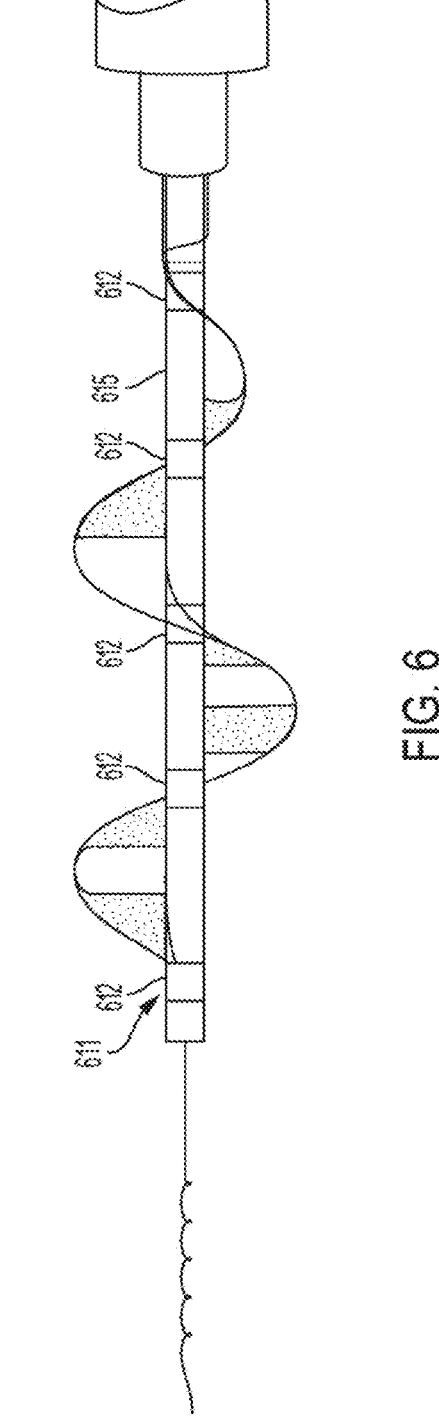
FIG. 6 illustrates a treatment system in accordance with aspects of the present technology.

In some embodiments, the coiled inner member 111 can be omitted or replaced with another suitable inner anchor configured to couple to the sheet of flexible material 117. For example, the coiled inner member 111 could be replaced with a hypotube, with a series of discrete tubular elements or rings, or other elements mounted over the core member with some degree of freedom. FIG. 6, for example, schematically illustrates a treatment system 600 similar to the treatment system 100 of FIG. 1, but with the inner member 611 comprising a plurality of discrete elements 612 axially spaced apart along the core member 615.

The dimensions described herein relate to a device for removing clot from leg veins or pulmonary arteries. However, these dimensions could all be changed to make devices of other sizes to treat other vessels. For example, instead of an 0.035" guidewire, the device could be designed for delivery over an 0.018", 0.014", or even a 0.010" guidewire.

Figure 2:
FIG. 2 illustrates a treatment device engaged with a blood clot in accordance with aspects of the present technology.

FIG. 2 illustrates clot material CM that is enveloped by the helical outer member 113 and baffles 121 that have been pulled proximally to help compress the clot material CM. The clot material CM is protected from distal embolization by the protective distal filter 123 and proximally is beginning to be compressed by the outer-most delivery sheath 105 in preparation for removal. The clot material CM may also be substantially elongated by the linearization of the helical outer member 113 and stretching of the coiled inner member 111 as it is withdrawn, which may substantially reduce the overall diameter of the clot material CM, allowing it to be more effectively drawn into the covering sheath 103 and/or the delivery sheath 105. As the helical outer member is linearized, the helical outer member and the coiled are pulled together into close apposition. The linear sheet of material, whose edges are formed by the helical outer member and coiled inner member, thereby forms a relatively closed tubular pouch, which serves to enclose and retain the clot material CM as it is withdrawn from the vessel.

Figures 3A, 3B:
FIG. 3A illustrates another embodiment of a treatment device in accordance with aspects of the present technology.
FIG. 3B illustrates a cross-sectional view of the helical outer member taken along line 3B-3B in FIG. 3A.

FIG. 3A illustrates an alternate embodiment of a treatment device 301 configured for removal of chronic fibrin-laden clots. In the illustrated embodiment, the treatment device 301 includes an integrally formed embolic protection filter or umbrella 303 at the distal end of the device 301. The helical outer member 305 can be similar to the helical outer member 113 described above, except the helical outer member 305 illustrated in FIG. 3A is coated in a durable polymer. As seen in the cross-section of FIG. 3B, the helical outer member 305 can have a smooth, curved radially outer surface 305a configured to abut the vessel wall and a less curved inner surface 305b, thereby providing a leading edge 305c and a trailing edge 305d at the junctions of the two surfaces which can help separate chronic clot from the wall of the vessel. In some embodiments, the helical outer member 305 can include only one of the edges 305c or 305d along some or all of its length. In some embodiments, the radially inward facing surface 305b is not planar but has some curvature, yet still provides a cutting edge 305c and/or 305d where the inward facing surface 305b joins the curved outer surface 305a. In some embodiments, the helical outer member 305 can include a ridge, protrusion, or other projecting element that forms a cutting member or cutting edge.

Such a cutting edge can be particularly useful in separating a chronic fibrin clot from a vessel wall, for example allowing the device to be used for an endovenectomy. In some instances, the helical outer member 305 can be urged forward and/or backward once in the expanded state such that the cutting edge is advanced axially into clot material. In some embodiments, the cutting edge may face only in one axial direction—e.g., only distally facing or only proximally facing at any point along the helical outer member 305 or along all of the helical outer member 305. In other embodiments, the outer helical member 305 can have one cutting edge facing distally and another cutting edge facing proximally, such that both proximal and distal movement of the helical outer member 305 enables the cutting edge to contact clot material.

In some embodiments, at the proximal portion of the helical coil is a unidirectional strut 307 which may be oriented proximally that is configured to open on removal of the covering sheath 103. This strut 307 may help to release the chronic clot from the wall and act as a "backstop" for the clot when the covering sheath 103 is being advanced prior to clot retrieval.

Figure 4:
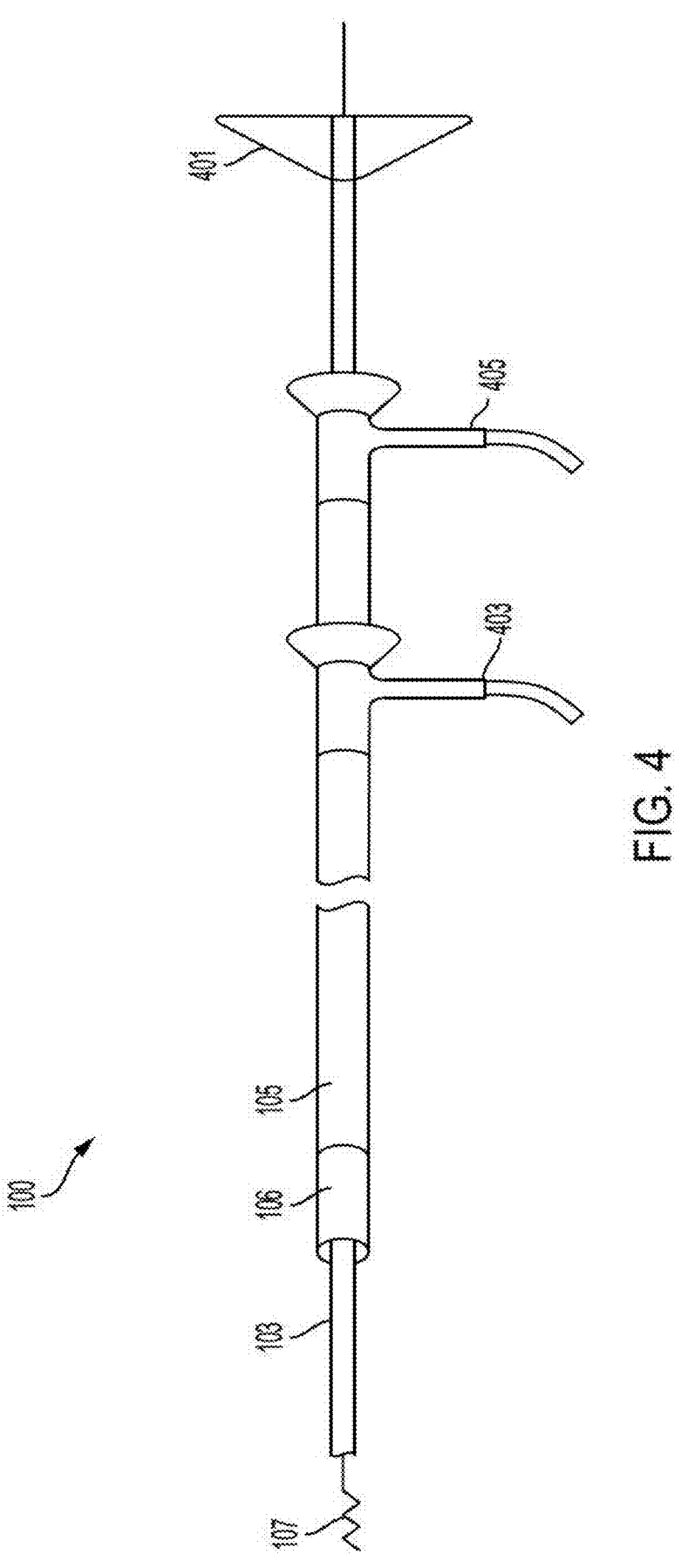
FIG. 4 illustrates the proximal end of the treatment system in accordance with aspects of the present technology.

FIG. 4 illustrates the proximal portion of the treatment system 100. As illustrated, a proximal portion of the treatment device 101 can extend proximally beyond proximal ends of the delivery sheath 105 and treatment catheter, allowing a clinician to manipulate the proximal end of the treatment system 100. At the proximal portion of the treatment system 100, a torque device 401 can engage the proximal portion of treatment device 101 to allow for some rotation of the device within the vessel to help orient the helical outer member 113 along the outer edge of the vessel and ensure maximum clot retrieval. In some embodiments, the torque device 401 can be permanently coupled to the proximal portion of the treatment device 101, while in other embodiments the torque device is removable.

Additionally, the proximal portion of the treatment system 100 can include a first hub 403 and a second hub 405 configured to be positioned external to the patient. The first and/or second hubs can be coupled to the delivery sheath 105 and/or the covering sheath 103, and can include a hemostatic adaptor, a Tuohy Borst adaptor, and/or other suitable valves and/or sealing devices. In some embodiments, the first and/or second hubs can further include an aspiration line coupled to a negative pressure-generating device, such as a syringe or a vacuum pump. Additionally, in some embodiments, the first and/or second hubs can include a port configured to receive one or more fluids before, during, and/or after the procedure (e.g., contrast, saline, etc.).

Example Methods of Operation

Prior to delivery, the treatment device 101 can be withdrawn into the covering sheath 103 for initial delivery into the vessel. This linearizes the helical outer member 113 such that it assumes the low-profile, compressed configuration. For a helix which has a pitch approximately equal to its diameter, this helix may elongate by over three times its length when it is linearized. When the helix is linearized in the covering sheath 103, the coiled inner member 111 can stretch by an equivalent length.

As an example, a procedure for using the treatment device can be as follows. First, the larger-diameter delivery sheath 105 is introduced into the vein or vessel. Then the treatment device 101 contained within the covering sheath 103 is introduced through the clot over a central guidewire. In some embodiments, the helical outer member 113 and/or the inner member 111 can include radiopaque markers or can be formed at least partially of radiopaque material to facilitate visualization under fluoroscopy. Once the distal end of the covering sheath 103 is past the clot, the covering sheath 103 is gradually withdrawn, allowing the helical outer member 113 to expand into the clot. It may be preferable to advance the treatment device somewhat as the covering sheath 103 is withdrawn, so that as the helical outer member 113 expands it resumes the desired pitch and diameter within the clot. The handle at the proximal end of the treatment device 101 may have a mechanism which simultaneously advances the treatment device 101 while retracting the covering sheath 103.

In some embodiments, the treatment device may be configured to expand within the blood clot and into apposition with the vessel wall. Once deployed, a slight twisting motion or advancement or retraction may allow for more complete deployment of the treatment device 101 with the outer edge of the polymer-wrapped helical outer member 113 abutting the vein wall throughout the length of the clot. The clot may be cut into a spiral shape by the expansion of the helical outer member 113, and since the strip of flexible material 117 extends from the helical outer member 113 to the coiled inner member 111, the clot will be engaged by this strip of flexible material 117.

Retrieval may then begin by pulling back proximally on the treatment device. The covering sheath 103 would move back with it, leaving the functional portion 109 of the treatment device out of the covering sheath 103. This retraction could be done manually or via a retraction handle at the hub of the catheter that would allow for precise tension on the helical outer member 113. In some embodiments, rather than pulling back the treatment device proximally, the covering sheath 103 and/or the delivery sheath 105 may be advanced distally over the treatment device 101 to recapture or resheath the treatment device 101.

As the helical outer member 113 and coiled inner member 111 are retracted into the larger delivery sheath 105, they will both lengthen and partially linearize as they are stretched. This will also begin to cause the helical outer member 113 to pull away from the vessel wall and draw closer to the coiled inner member 111. The baffles 121 in the flexible material 117 between the coiled inner member 111 and the helical outer member 113 would then tend to engage the blood clot and begin to linearize the spiral clot to facilitate retrieval. The treatment device may then be slowly withdrawn into the larger delivery sheath 105. The helical outer member 113, the polymer baffles 121, and the closed-cell polymer embolic-protection filter 123 each facilitate drawing the clot into the delivery sheath 105. The delivery sheath 105 could alternatively be advanced forward as the clot is captured, such that the expanding tip could help to further capture and compress the retrieved clot. The treatment device 101 and covering sheath 103 could then be completely withdrawn through the delivery sheath 105, or both the covering sheath 103 and the delivery sheath 105 with the treatment device 101 could then be removed through a larger access sheath over a wire, thus completing clot retrieval. The device could be cleaned and re-housed to allow for multiple treatment passes to be made.

Example Methods of Manufacturing

Figure 5:
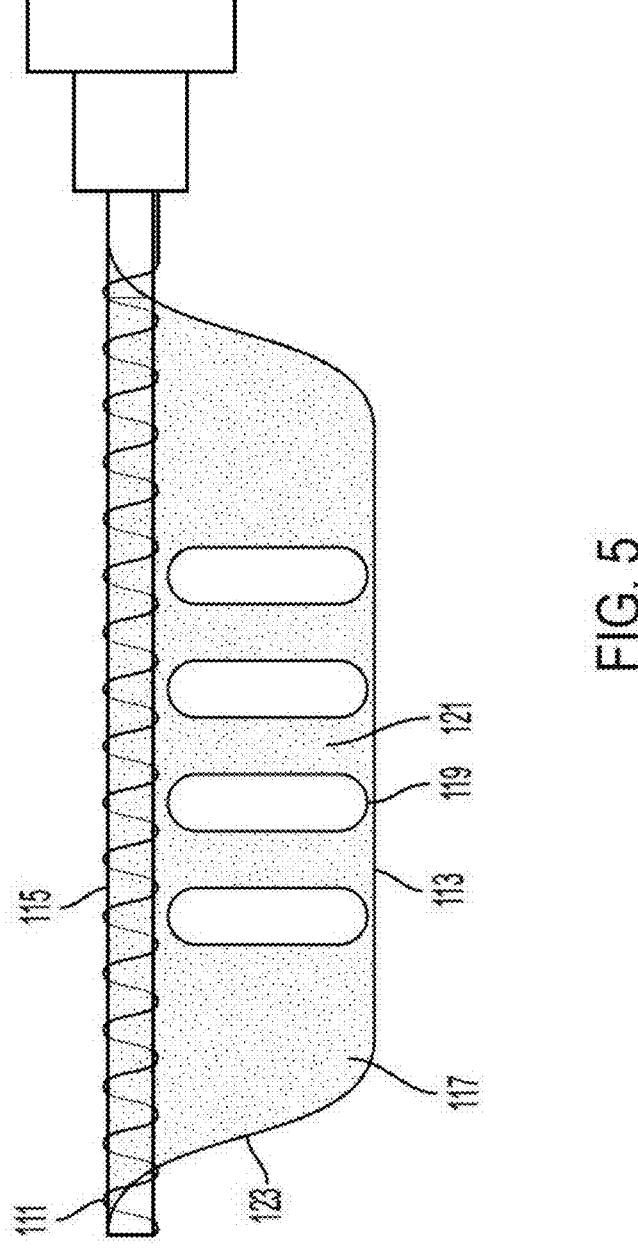
FIG. 5 illustrates a method of manufacturing a treatment device in accordance with aspects of the present technology.

FIG. 5 illustrates a manufacturing process for the functional section 109 of the treatment device. A helical outer member 113 (e.g., a wire or other elongated structure) is formed into the desired helical shape and bonded to a coiled inner member 111 at its proximal and distal end portions, for example via soldering, welding, adhesives, or other suitable fixation technique. Then this assembly can be twisted and pulled lengthwise to unwind the helix and straighten it, and the straightened helix is held in a fixture parallel to and an appropriate distance away from the coiled inner member 111, as depicted in FIG. 5. A polymer tube may then be run through the lumen of the coiled inner member 111. In some embodiments, a Teflon blocker tube may be inserted into the center lumen of this polymer tube to ensure an inner guidewire lumen diameter of at least approximately 0.040" to facilitate passage of an 0.035" or 0.038" guidewire.

A sheet of flexible material 117 can then be wrapped around the helical outer member 113 and the coiled inner member 111 and sealed in place. The sheet 117 may be fused to itself as well as to the core member 115 to hold the assembly together. After the sheet 117 is fused, it can be trimmed and any desired slotting, baffling, twisting, cupping, perforating, or other processing of the polymer sheet can be performed to optimize its clot-engagement capabilities.

When this assembly is released from the fixture, it returns to its helical shape around the coiled inner member 111, which forms a shape suitable for clot retrieval as described above. The distal aspect of the polymer may remain in a closed-cell fashion without baffles to provide a distal embolic filter 123. The proximal end of the assembly may then be attached to the shaft of the treatment device 101, for example by inserting and bonding the proximal extension of the coiled inner member 111 and/or the helical outer member 113 into the shaft of the treatment device 101.

The oval windows 119 seen in FIG. 5 are examples of cut windows that allow for the remaining polyurethane "bridges" to act as baffles 121 that can engage and compress a clot when tension is pulled on the proximal end of the treatment device, straightening the helical outer member 113 and stretching the coiled inner member 111. Various other patterns of cuts, perforations, slices, or other openings can be provided to tailor performance of the remaining flexible material 117 in engaging clot material.

Conclusion

Although many of the embodiments are described above with respect to systems, devices, and methods for treatment of pulmonary embolisms, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-5.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A device comprising a distal portion for treatment of deep vein thrombosis or pulmonary embolism, the device comprising:

an elongated member configured to be positioned intravascularly at or adjacent to a treatment site comprising clot material;

a cutting member disposed at the distal portion, the cutting member having a low-profile configuration for delivery through a catheter and an expanded configuration for deployment at the treatment site, the cutting member comprising a cutting edge and a sheet of flexible material extending towards and coupled to the elongated member such that, when the cutting member is deployed in the expanded configuration, the sheet of flexible material forms a spiral helical strip and the cutting edge is configured to engage the clot material to facilitate clot retrieval; and a filter disposed at the distal portion distal to the cutting member, the filter configured to prevent distal embolization of the clot material dislodged by the cutting member, wherein a radial dimension of the elongated member does not change as the cutting member transitions between the low-profile configuration and the expanded configuration.

2. The device of claim 1, wherein the sheet of flexible material comprises a flexible metal.

3. The device of claim 1, wherein the elongated member comprises a tube configured to be slidably advanced over a guidewire.

4. The device of claim 1, further comprising the filter comprises a flexible material.

5. The device of claim 1, wherein the filter is a closed-cell filter.

6. The device of claim 1, wherein the cutting member comprises a helical outer member spirally winding around and surrounding a portion of the elongated member.

7. The device of claim 6, further comprising a torque device at a proximal portion of the device to allow rotation of the device within the vessel to orient the helical outer member.

8. The device of claim 1, wherein the elongated member comprises a coil.

9. The device of claim 1, wherein the elongated member comprises a hypotube.

10. The device of claim 1, wherein a distal end portion of the cutting member is moveable relative to a proximal end portion of the cutting member to transition the cutting member between the low-profile configuration and the expanded configuration.

11. The device of claim 10, wherein the distal end portion of the cutting member is moveable relative to the proximal end portion by having the distal end portion and the proximal end portion move closer together or further apart.

12. A device for treatment of deep vein thrombosis or pulmonary embolism, the device comprising:

a core member configured to be positioned intravascularly at or adjacent to a treatment site comprising clot material;

an inner member disposed over the core member; and a helical outer member spirally winding around and surrounding a portion of the inner member, the helical outer member having a low-profile configuration for delivery through a catheter and an expanded configuration for deployment at the treatment site, the helical outer member comprising a cutting edge and a sheet of flexible material extending towards and coupled to the inner member such that, when the helical outer member is deployed, the sheet of flexible material forms a spiral helical strip and the cutting edge of the helical outer member is configured to engage the clot material to facilitate clot retrieval, wherein a distal end portion of the helical outer member is moveable relative to a proximal end portion of the helical outer member to transition the helical outer member between the low-profile configuration and the expanded configuration.

13. The device of claim 12, wherein the core member comprises a tube configured to be slidably advanced over a guidewire.

14. The device of claim 12, wherein the sheet of flexible material is configured to engage clot material when the helical outer member is in the expanded configuration.

15. The device of claim 12, wherein a distal portion of the device defines an expandable closed-cell filter.

16. The device of claim 15, wherein the closed-cell filter is configured to prevent distal embolization of clot material.

17. The device of claim 2, wherein the sheet of flexible material comprises a flexible metal.

18. The device of claim 12, wherein the inner member is configured to transition from a first axial length to a second axial length greater than the first axial length.

19. The device of claim 12, wherein, when the helical outer member transitions from the low-profile configuration to the expanded configuration, the distal end portion and the proximal end portion move closer together.

20. The device of claim 12, wherein the helical outer member comprises stainless steel or nitinol.

21. The device of claim 12, wherein the helical outer member has a radially outer surface configured to abut a vessel wall and the cutting edge comprises a sharp edge configured to engage clot material.

22. The device of claim 21, wherein the sharp edge is configured to facilitate separating the clot material from the vessel wall.

23. The device of claim 12, further comprising a torque device at a proximal portion of the device to allow rotation of the device within the vessel to orient the helical outer member.

* * * * *